United States Patent [19]

Griggs

[11] Patent Number: 5,279,285
[45] Date of Patent: Jan. 18, 1994

[54] TRACHEOSTOMY METHOD AND APPARATUS

[76] Inventor: William M. Griggs, 15 Avenel Gardens Road, Medindle, South Australia, 5081

[21] Appl. No.: 853,720
[22] PCT Filed: Dec. 7, 1990
[86] PCT No.: PCT/AU90/00583
§ 371 Date: Jul. 16, 1992
§ 102(e) Date: Jul. 16, 1992
[87] PCT Pub. No.: WO91/08709
PCT Pub. Date: Jun. 27, 1991

[30] Foreign Application Priority Data

Dec. 11, 1989 [AU] Australia ............... PJ 7792

[51] Int. Cl.⁵ ............................................. A61M 16/00
[52] U.S. Cl. .......................... 128/200.26; 128/207.14; 128/207.29
[58] Field of Search ............... 128/200.26, 207.29, 128/207.14, 207.15

[56] References Cited

U.S. PATENT DOCUMENTS

| | | | |
|---|---|---|---|
| 3,511,243 | 5/1970 | Toy | 128/207.29 |
| 3,613,684 | 10/1971 | Sheridan | 128/207.29 |
| 3,704,529 | 12/1972 | Cioppa | 128/207.29 |
| 3,817,250 | 6/1974 | Weiss | 128/207.29 |
| 3,841,334 | 10/1974 | Wolf | 128/207.29 |
| 4,239,042 | 12/1980 | Asai | 128/207.29 |
| 4,364,391 | 12/1982 | Toye | 128/207.29 |
| 4,405,314 | 9/1983 | Cope | 128/207.29 |
| 4,471,778 | 9/1984 | Toye | 128/207.29 |
| 4,520,810 | 6/1985 | Weiss | 128/200.26 |
| 4,677,978 | 7/1987 | Melker | 128/207.29 |
| 4,693,250 | 9/1987 | Coons | 606/198 |
| 4,889,112 | 12/1989 | Schachner et al. | 128/200.26 |
| 5,186,168 | 2/1993 | Spofford et al. | 128/200.26 |
| 5,217,005 | 6/1993 | Weinstein | 128/200.26 |
| 5,217,007 | 6/1993 | Ciaglia | 128/200.26 |

FOREIGN PATENT DOCUMENTS

| | | |
|---|---|---|
| 46581/72 | 3/1974 | Australia . |
| 2036538 | 12/1970 | France . |
| WO87/05792 | 10/1987 | World Int. Prop. O. . |
| WO91/08709 | 6/1991 | World Int. Prop. O. . |

OTHER PUBLICATIONS

*Percutaneous Tracheostomy–A New Method*, published in Critical Care Medicine, vol. 17, No. 10, 1989 by A. Schachner, Y. Ovil, J. Sidi, M. Rogev, Y. Heilbronn, and M. J. Levy.

Primary Examiner—Edgar S. Burr
Assistant Examiner—Aaron J. Lewis

[57] ABSTRACT

This invention relates to the field of tracheostomy and resides in a method of inserting a tracheostomy tube into the trachea of a patient. The method includes the steps of inserting a hollow needle into the trachea, sliding a cannula over the needle into the trachea, withdrawing the needle, threading a guide wire through the cannula and passing the wire into the trachea. The guide wire is extended in the trachea towards the lungs of the patient. The cannula is removed from the wire, leaving the wire is place, and a dilator instrument in threaded over the wire. The instrument is slid along the wire until it extends into the trachea. The instrument has jaws which may be separated once within the trachea to split the trachea, and the jaws are curved so that the jaws can extend into the trachea and extend down the trachea. Spreading the jaws splits the trachea wall through which the jaws are inserted transversely, allowing the removal of the instrument while leaving the wire in the trachea. A tracheostomy tube can be threaded along the wire into the trachea and then the wire is removed.

2 Claims, 2 Drawing Sheets

TRACHEOSTOMY METHOD AND APPARATUS

This invention relates to the field of tracheostomy and more particularly relates to a method and apparatus whereby a tracheostomy tube may be inserted into the trachea of a patient in a minimum of time and with a minimum risk of secondary injury.

The term patient will be used in this specification in a general sense but may include human or animal subjects.

The surgical procedure of tracheostomy has often to be carried out in emergency situations and thus the operation ideally should be completed in a minimum amount of time. While emergency airway access can be accomplished by making an incision into the trachea the more permanent tracheostomy requires the incision into the trachea to receive a tracheostomy tube which has an inflatable cuff which is inflated after insertion to seal the tube in the trachea so that inspiration and expiration of air is all accomplished by use of the tracheostomy tube.

A number of percutaneous tracheostomy techniques have been described to perform a tracheostomy easily and rapidly for instance at a bedside but many of these have been slow, difficult to perform and/or had a significant likelihood of secondary injury such as injury to the of the trachea at points other than where the incision is made. In general the process requires the forming of a hole in the wall of the trachea by splitting it laterally between the tracheal rings. In the past this has been achieved by the use of a number of dilators of increasing diameter but this process has taken some time and actually on occasion some secondary injury to the trachea because longitudinal as well as lateral forces are applied by such devices.

This present invention proposes an alternative arrangement which will provide substantially lateral splitting between the tracheal rings while providing a minimum risk of secondary damage to the trachea.

In one form the invention is said to reside in a method of inserting a tracheostomy tube into the trachea of a patient, the method including the steps of inserting a hollow needle into the trachea, sliding a cannula over the needle into the trachea withdrawing the needle, threading a guide wire through the cannula and passing the wire into the trachea to extend in the trachea towards the lungs of the patient, removing the cannula and leaving the wire in place, threading a dilator instrument over the wire and sliding the instrument along the wire until it extends into the trachea, the instrument having jaws which may be separated once within the trachea to split the trachea and the jaws being curved so that the jaws can extend into the trachea and extend down the trachea, spreading the jaws to split the trachea wall through which the jaws are inserted transversely, removing the instrument while leaving the wire in the trachea, threading a tracheostomy tube along the wire into the trachea and removing the wire.

Also there is provided according to the invention a tracheostomy instrument for use in the above described method, the instrument comprising a pair of members pivoted to each other intermediate their ends, one end of each of the members being formed as a jaw to cooperate with the jaw of the other member, the pair of jaws being curved, each of the jaws having on a cooperating face a groove extending from the end of the jaw along at least part of the length of the jaw and terminating in an opening on the side of the jaw, the grooves on the two jaws cooperating when the jaws are in a closed position to provide a passage such that a wire can be threaded therethrough, the other end of the members each providing a handle and means to engage each other to lock the jaws in the closed position.

In one preferred embodiment of the invention the members are pivoted together such that moving the handle ends together moves the jaw ends together. Alternatively the instrument may be constructed so that the members are pivoted together such that moving the handle ends together moves the jaws ends apart.

The curve of the jaws may be up to 90°.

Preferably the jaws are tapered towards their ends.

The means to engage the handles may comprise cooperating ratchet parts on each handle.

The jaws may further have rounded ends so as to provide minimal damage to the interior of the trachea.

In one preferred embodiment one or more tubular dilators can be threaded over the wire to enlarge the incision before the insertion of the instrument.

The instrument for ease of description can be described as being similar to a pair of forceps the instrument having jaw curved along their longitudinal axis and on the cooperating faces of each jaw there is provided a groove extending from the end of the jaws back along the jaws and then opening to one side of the jaws. The instrument may be locked by its ratchet or other locking means in the closed position and then the instrument can be threaded over the wire and into the incision in the trachea. The handles of the instrument are then operated to unlock the ratchet or other locking mechanism and the jaws are then spread to dilate the incision transversely between tracheal rings while not making significant longitudinal movement.

This then generally describes the invention but to assist with understanding of the invention reference will now be made to the accompanying drawings which show preferred embodiments of the invention.

In the drawings

Figure 1:
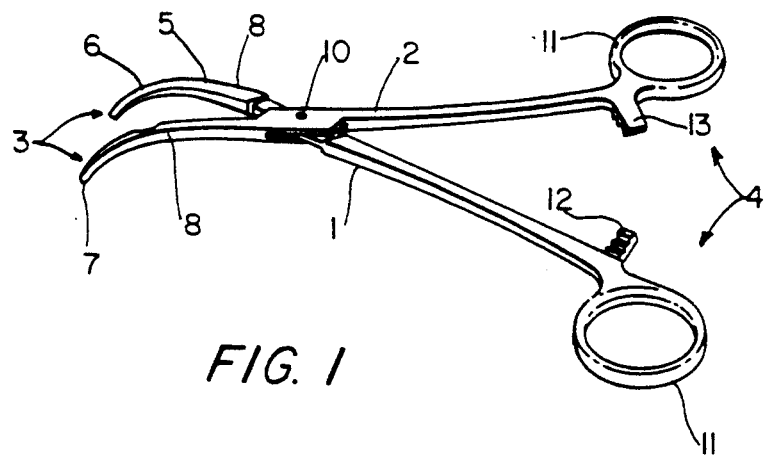
FIG. 1 shows a first embodiment of an instrument according to this invention.

Now looking more closely at the drawings and in particular FIG. 1 it will be seen that the instrument comprises members 1 and 2 each of which have a jaw end 3 and a handle end 4. The jaw end 3 has jaws 8 with a cooperating face 5 along which extends a groove 6. The jaws 8 are curved along their longitudinal axis and terminate in a rounded tip 7. A pivot 10 is provided intermediate the ends of the members 1 and 2 and extending away from the jaws opposite the pivot are the handle ends 4 terminating in handles 11. The handle ends also include cooperating ratchet parts 12 and 13 which enable the instrument to be locked with the jaws in the closed position so that the groove 6 in each jaw part 8 cooperate to form a passage through which a dilation wire may be passed.

The instrument is constructed in this embodiment such that moving the handles together moves the jaws together.

Figure 2:
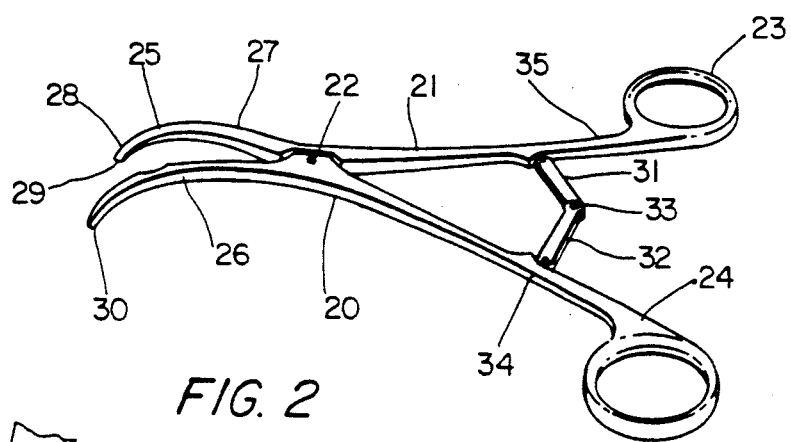
FIG. 2 shows a second embodiment of an instrument according to this invention.

FIG. 2 shows an alternative embodiment of tracheostomy instrument according to the invention. In this invention the two members 20 and 21 are pivoted at point 22 such that the handle ends 23 and 24 are moved apart the jaw ends 25 and 26 are moved together. The jaw ends 25 and 26 include cooperating faces such as the face 27 on the jaw 25 and a groove 28 in the cooperating face. It may be particularly noted that the jaws 27 and 26 are curved along their length so that when the tracheostomy instrument is inserted into the trachea while the instrument may extend directly out from the trachea the tips of the jaws 29 and 30 extend down the trachea and as the jaws are spread they will do minimum damage to the inside walls of the trachea.

The locking arrangement of the embodiment shown in FIG. 2 comprises a pair of arms 31 and 32 pivoted at their joining parts at 33 and pivoted at 34 and 35 to the handle ends 24 and 23 respectively and this pivot arrangement may include an over centre locking arrangement so that as the handles are moved apart the jaws are moved closer together and the locking arrangement locks them in this closed position. The advantage of the embodiment shown in FIG. 2 is that spreading the jaws is achieved by moving the handle ends closer together and hence there is a limit to the amount of spreading which can be achieved.

Now looking at FIGS. 3 to 8 one embodiment of a method of performing a percutaneous tracheostomy will be discussed.

The percutaneous tracheostomy is usually performed while the patient is receiving either general anaesthesia or local anaesthesia. The patient may be positioned with a pillow or sand bag under the shoulders to increase the extension of the neck.

Figure 3:
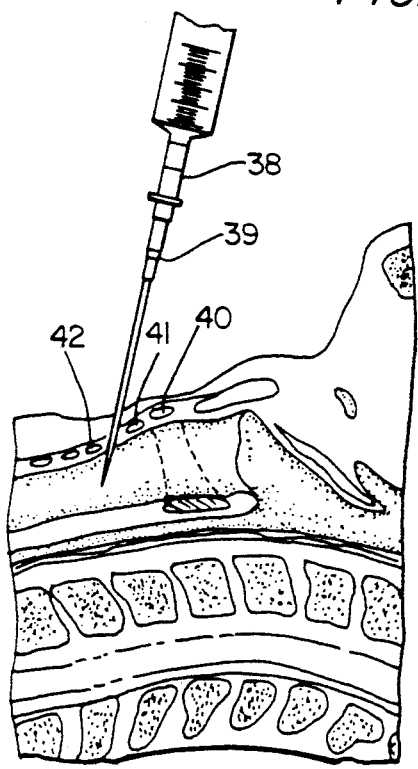
FIGS. 3 to 8 show the various stages of insertion of a tracheostomy tube into a patient according to this invention.
Figure 4:
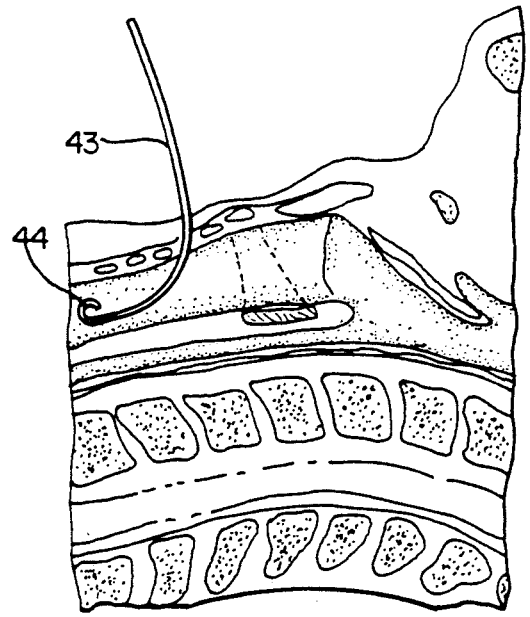

A first stage is to locate the cricoid cartilage 40. A mid-line traverse percutaneous incision of approximately 1.5 to 2 cm in length is made immediately below the level of cricoid cartilage. An intravenous needle 38 and cannula 39 with an attached fluid filled syringe is inserted in the mid-line of the incision and directed posterially while withdrawing the plunger of the attached syringe as shown in FIG. 3. The needle is directed to pass between the cricoid and first tracheal ring 41 or between the first tracheal ring 41 and the second tracheal ring 42. As soon as air begins to bubble into the syringe the outer plastic cannula is advanced into the lumina of the trachea and the inner needle is removed. A guide wire 43 preferably with a J-tip 44 is introduced into the trachea through the plastic cannula and then the plastic cannula is removed leaving the guide wire in place as shown in FIG. 4. The use of the plastic cannula avoids the risk of advancing the needle through the back wall of the trachea during wire insertion.

Figure 5:
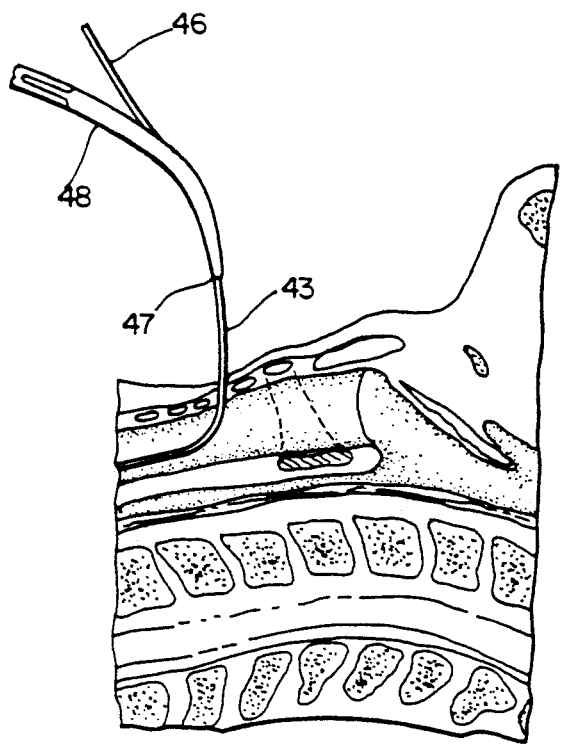
Figure 6:
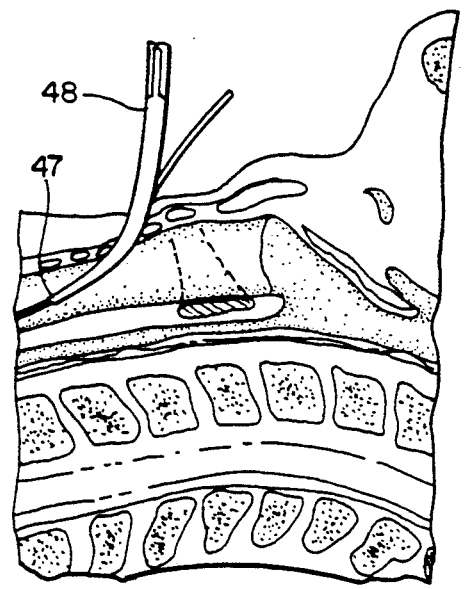
Figure 7:
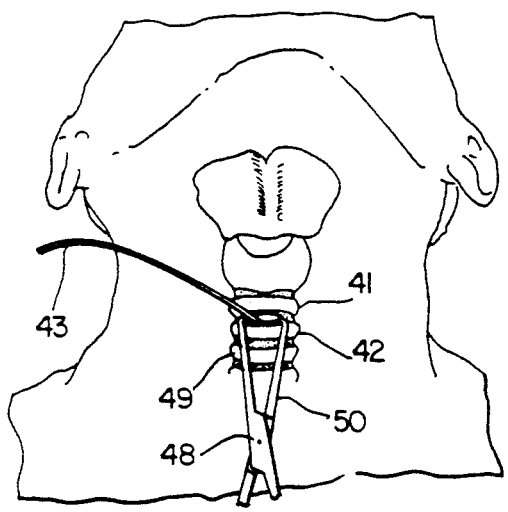
Figure 8:
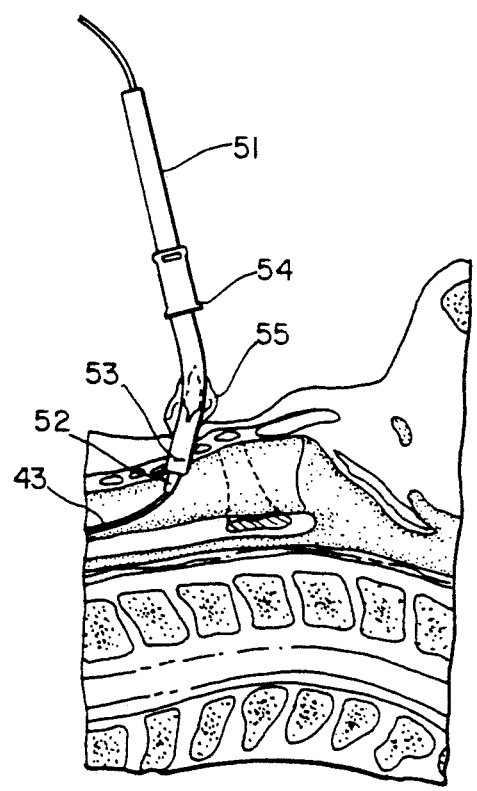

As shown in FIG. 5 the end 46 of the guide wire is passed in to the tip of 47 of the tracheostomy dilation instrument 48 and passed up through the passage formed into the jaws of the instrument. The forceps are then advanced along the wire through the soft tissues of the neck until the tip 47 passes into the trachea and then the instrument 48 is rotated so that the tip 47 is directed down the trachea in substantially the centre of the trachea as shown in FIG. 6. The handles of the instrument 48 are then moved to open the jaws to substantially the same diameter as the skin incision to split the wall of the trachea between two tracheal rings. This can be particularly seen in FIG. 7 which is shown partially in cut away view where the jaws 49 and 50 of the instrument 48 have been spread between tracheal rings 41 and 42 so that a transverse split is made without longitudinal damage to the trachea. The guide wire 43 remains in the trachea.

The forceps 48 are then removed with the guide wire 43 remaining in the trachea and extending down the trachea. A tracheostomy tube 51 is then threaded over the guide wire 43 preferably with a trocar 52 or internal guide so that the tip 53 of the tracheostomy tube 51 passes along the wire and down the trachea. Once the tracheostomy tube is inserted into the trachea down to the hilt 54 then the cuff 55 is inflated by means not shown and the appropriate breathing circuit is connected.

Through this invention the inventions have provided a method and an instrument which simplifies the process of percutaneous tracheostomy and provides less risk of secondary injury particularly owing to the curved nature of the instrument jaws so that during the dilation procedure the ends of the jaws lie in the long axis of the trachea and there is less risk of secondary damage to the lateral or posterior tracheal walls.

I claim:

1. A method of inserting a tracheostomy tube into the trachea of a patient, the method including the steps of, inserting a needle into the trachea, sliding a cannula over the needle into the trachea, withdrawing the needle, threading a guide wire through the cannula and passing the wire into the trachea to extend within the trachea towards the lungs of the patient, removing the cannula and leaving the wire in place, threading a dilation instrument over the wire and sliding the instrument along the wire until it extends into the trachea, the instrument having jaws which may be separated once within the trachea to dilate the trachea and the jaws being curved so that the jaws can extend into the trachea and extend down the trachea, spreading the jaws to dilate the trachea wall through which the jaws are inserted, removing the instrument while leaving the wire in the trachea, threading a tracheostomy tube along the wire and into the trachea, and removing the wire.

2. A method as in claim 1 further including the step of threading a dilation catheter onto the guide wire before insertion of the dilation instrument.

* * * * *